US008647689B2

(12) United States Patent
Vanhemelrijck et al.

(10) Patent No.: US 8,647,689 B2
(45) Date of Patent: Feb. 11, 2014

(54) CITRUS FRUIT FIBERS IN EMULSIONS

(75) Inventors: Jozef Guido Roza Vanhemelrijck, Meise (BE); Catharina Hillagonda McCrae, Bertem (BE)

(73) Assignee: Cargill, Incorporated, Wayzata, MN (US)

( * ) Notice: Subject to any disclaimer, the term of this patent is extended or adjusted under 35 U.S.C. 154(b) by 850 days.

(21) Appl. No.: 11/993,347

(22) PCT Filed: Jul. 3, 2006

(86) PCT No.: PCT/EP2006/006442
§ 371 (c)(1),
(2), (4) Date: Dec. 20, 2007

(87) PCT Pub. No.: WO2007/003391
PCT Pub. Date: Jan. 11, 2007

(65) Prior Publication Data
US 2010/0196519 A1    Aug. 5, 2010

(30) Foreign Application Priority Data
Jul. 6, 2005  (EP) .................................. 05254253

(51) Int. Cl.
*A61K 36/752* (2006.01)
*A23L 1/00* (2006.01)

(52) U.S. Cl.
USPC ............... 426/73; 426/72; 426/311; 426/616; 426/569; 424/736; 424/725; 424/401

(58) Field of Classification Search
USPC .............. 426/72, 311, 616, 569, 73; 424/725, 424/736, 401
See application file for complete search history.

(56) References Cited

U.S. PATENT DOCUMENTS

| | | | |
|---|---|---|---|
| 4,413,017 A | 11/1983 | Loader | |
| 4,623,549 A | 11/1986 | Katt et al. | |
| 4,774,099 A | 9/1988 | Feeney et al. | |
| 4,865,863 A | 9/1989 | Prosise et al. | |
| 5,162,128 A | 11/1992 | Mills et al. | |
| 5,458,904 A | 10/1995 | Zolper | |
| 5,725,899 A | 3/1998 | Cole et al. | |
| 6,503,545 B1 * | 1/2003 | Perlman et al. | 426/72 |
| 2004/0258801 A1 * | 12/2004 | Ling et al. | 426/72 |
| 2005/0271790 A1 | 12/2005 | Aronson et al. | |
| 2006/0115564 A1 | 6/2006 | Passarelli et al. | |
| 2006/0251789 A1 | 11/2006 | Lundberg et al. | |
| 2006/0280840 A1 | 12/2006 | Robertson | |
| 2010/0196519 A1 | 8/2010 | Vanhemelrijck et al. | |
| 2011/0020525 A1 | 1/2011 | Homsma et al. | |
| 2011/0293814 A1 | 12/2011 | Alexandre et al. | |

FOREIGN PATENT DOCUMENTS

| | | |
|---|---|---|
| DE | 199 43 188 | 3/2001 |
| EP | 0 485 030 | 11/1991 |
| EP | 0 966 889 | 6/1999 |
| EP | 1723856 A1 | 11/2006 |
| JP | S62036149 A | 2/1987 |
| JP | 2006014629 | 1/2006 |
| RU | 2156594 * | 9/2000 |
| RU | 2277354 | 6/2006 |
| WO | WO01/17376 | 3/2001 |
| WO | WO02/15720 | 2/2002 |
| WO | WO2005/034653 | 4/2005 |
| WO | WO2005/034654 | 4/2005 |
| WO | WO 2006/033697 | 3/2006 |
| WO | WO2006/122734 | 11/2006 |
| WO | 2007/003391 | 1/2007 |
| WO | 2008/062057 A | 5/2008 |
| WO | WO2009/075851 | 6/2009 |
| WO | 2010093864 A3 | 11/2010 |

OTHER PUBLICATIONS

Grigelmo-Miguel et al. Characterization of Dietary Fiber From Orange Juice Extraction; Food Research International, vol. 31, No. 5, pp. 355-361.*
Porzio et al. Washed Orange Pulp; Characterization and Properties; ACS Symposium Series, Apr. 11, 1983, pp. 191-204.*
Souci et al., "Food compositions and nutrition tables," *Medpharm.*, 2000, p. 47.
PCT International Search Report from corresponding PCT/US2010/024015 mailed Sep. 21, 2010. 3 pages.
PCT International Search Report from corresponding PCT/EP2006/006442 mailed Jul. 9, 2006. 2 pages.
PCT International Search Report from corresponding PCT/US08/13579, mailed Feb. 26, 2009, 1 page.
English abstract of Japanese patent No. JPS62036149 A, Feb. 17, 1987. 2 pages.
Machine Translation of Kazutoshi JP 2006-014629 (Jan. 2006).
Cengiz E et al., "Changes in energy and cholesterol contents of frankfurter-type sausages with fat reduction and fat replacer addition", Food Chemistry, Jul. 1, 2005, vol. 91, No. 3, pp. 443-447, Elsevier Ltd, NL.
Larrea M A et al., "Some functional properties of extruded orange pulp and its effect on the quality of cookies", Lebensmittel VVissenschaft und Technologies, May 1, 2005, pp. 213-220, vol. 38, No. 3, Academic Press, London, GB.

(Continued)

*Primary Examiner* — Patricia Leith

(57) ABSTRACT

The current invention relates to a composition of citrus fruit fibers and hydrophobic vitamin. The hydrophobic nutritional supplement is selected from the group consisting of vitamin A, D, E, K, and mixtures thereof. It further relates to a process for preparing liquid compositions comprising said citrus fruit fibers and hydrophobic vitamin. Furthermore it relates to beverages comprising said composition.

12 Claims, No Drawings

(56) References Cited

OTHER PUBLICATIONS

Fisher, J., "Functional Properties of Herbacel AQ Plus Fruit Fibers"; Poster presented at Dietary Fibre 2000, Dublin, May 13-18, 2000, 2 pages.

Yoshida et al., "Citrus Juice Waste as a Potential Source of Dietary Fiber", J. Japan Soc. Hort. Sci., vol. 53, No. 3, pp. 354-361, 1984.

"Reduce Fat with Pulp Fiber", Prepared Food Networks, [Online}, retrieved from: http://www.preparedfoods.com/articles/reduce-fat-with-pulp-fiber, accessed Aug. 12, 2011, 2 pages.

\* cited by examiner

US 8,647,689 B2

CITRUS FRUIT FIBERS IN EMULSIONS

CROSS-REFERENCE TO RELATED APPLICATIONS

This application is a National Stage application under 35 U.S.C. §371 of International Application No. PCT/EP2006/006442 having an International Filing Date of Jul. 3, 2006, which claims the benefit of priority of EP 05254253.7 having a filing date of Jul. 6, 2005.

TECHNICAL FIELD

The current invention relates to a composition of citrus fruit fibers and hydrophobic vitamin. It further relates to a process for preparing liquid compositions comprising said citrus fruit fibers and hydrophobic vitamin.

BACKGROUND OF THE INVENTION

Food manufacturers are continuously challenged to find ways to present an appetizing and authentic food product at minimized raw material costs. One area of particular endeavor has been the goal of producing liquid compositions including hydrophobic nutritional supplements and particularly hydrophobic vitamins.

One of the problems encountered by beverages manufacturers is commonly called "Ringing". This term is used to illustrate the formation of a separate fat-soluble vitamin layer on the top of the liquid; unfortunately vitamin formulations have not solved this problem. One means of adding fat-soluble vitamins to beverages without ringing is to encapsulate the vitamins in liposomes. However, this is a costly process, and the concentration of active substance in the liposome tends to be low.

Another solution has been provided by EP 0 966 889 which pertains to modified polysaccharide matrix in which droplets of fat soluble vitamin having an average about 70 to 200 nanometers in diameter. The use of such matrix in beverages is disclosed.

However, this process implies chemical modification of the polysaccharide and also a precise determination of the vitamin droplets size.

As apparent from the art, the known processes are not cost efficient or involve chemically modified compounds, which are not well perceived by the consumers, and even with such compounds the used processes are still complex.

The emulsifying properties of "clean label" compounds have already been investigated in the art, for example in DE 199 43 188 A1. In this document, a fruit juice composition containing dietary fibers and buttermilk is disclosed. Buttermilk is the aqueous material released by the churning of milk-cream and is usually used in the food industry for its emulsifying properties due to its high protein content.

Dietary fibers are in this case used, after a specific treatment, due to its high water binding capacity.

EP 0 485 030 discloses a juice comprising optionally from 0.002 to about 1% aqueous and oil essence or other flavorant. In this application, the aqueous essence is a water-soluble component and the essence oil is the oily fraction. This juice contains citrus fibers and a residual portion of intrinsic essence oil that is exhibited during the concentration of said juice.

One problem with such process is that the addition of the finely divided citrus fiber should be conducted at low-shear and must not be followed by any further high shear operations prior to packing otherwise the beverage becomes too viscous or even gelled.

Thus, there is currently still a need of having high quality "clean-label" liquid compositions comprising hydrophobic vitamins.

The current invention provides such a product and process for preparing it.

Indeed, the inventors have surprisingly found that the hydrophobic vitamins can be included in aqueous liquid medium while being stabilized and protected (from oxidation) by citrus fiber.

SUMMARY OF THE INVENTION

The current invention relates to a liquid composition comprising an edible liquid, citrus fruit fiber and hydrophobic vitamin; the edible liquid being water or a water miscible liquid.

The citrus fruit fiber is having a total dietary fiber content of from 60 to 85-wt % (dry weight) and a water binding capacity of from 7 to 25 (w/w). The citrus fruit fiber is comprising up to 10% (w/w) proteins.

In one embodiment, citrus fiber has a total dietary fiber content of from 60 to 80-wt % and a water binding capacity of from 7 to 12 (w/w).

Furthermore the citrus fruit fiber is obtainable from citrus fruit selected from the group consisting of oranges, tangerines, limes, lemons and grapefruit.

In a preferred embodiment the citrus fiber used is orange pulp fiber.

The hydrophobic vitamin is selected from the group consisting of vitamin A, D, E, K and mixtures thereof. The vitamin preferably included is vitamin E. Said composition can further comprise edible additives.

In a preferred embodiment, the citrus fiber is in dry form before being added to the edible liquid.

Furthermore, the current invention relates to a process for preparing a liquid composition comprising an edible liquid, citrus fruit fiber and hydrophobic vitamin and said process comprises:
 a. Adding dry citrus fruit fiber to an edible liquid to form a liquid mixture,
 b. Adding the hydrophobic vitamins to the liquid mixture,
 c. Treating mechanically the liquid mixture.

Also part of this invention is a composition where the ratio of citrus fruit fiber to hydrophobic vitamin is from about 1:0.001 to about 1:35. A preferred composition comprises from 0.001 to about 5 percent by weight of citrus fruit fiber.

The current invention relates to the use of the currently disclosed liquid composition in food applications, feed applications, pharma products or cosmetics.

The current invention further relates to beverages comprising citrus fruit fiber and hydrophobic vitamins.

DETAILED DESCRIPTION

The current invention relates to a liquid composition comprising an edible liquid, citrus fruit fiber and hydrophobic vitamin. Citrus fiber is a valuable component, which has relatively high total dietary fiber content and a balanced ratio of soluble to insoluble dietary fiber. For example, the total dietary fiber preferably is made up of about 45-50% soluble dietary fiber and from 50-55% insoluble dietary fiber.

The balanced dietary fiber spectrum insoluble (structural) and soluble (chiefly pectin) fiber is advantageous in physiological functionality over cereal-based fibers. Citrus fiber, particularly orange fiber, more in particular dried citrus fruit fiber; has an extremely high water binding capacity, resulting in high viscosities compared to other citrus fibers such as Vitacel™ orange fiber (available from Rettenmaier). In one preferred embodiment, dried citrus fiber has a total dietary content of from about 60 to about 85-wt % (based on dry substance) and a water binding capacity from 7 to about 25 (w/w). Preferably the total dietary fiber content is at least about 70-wt % and the water binding capacity is at least about 8 (w/w).

The citrus fiber is extracted from citrus vesicles from a wide variety of citrus fruits, non-limiting examples of which include oranges, tangerines, limes, lemons and grapefruit.

Citrus vesicles refer to the cellulosic material contained in the inner, juice-containing portion of citrus fruit. Citrus vesicles are sometimes also referred to as coarse pulp, floaters, citrus cells, floating pulp or pulp.

In contrast, citrus flour obtained from citrus peel is characterized by an orange peel taste and odor, and a dark orange color, which is severely limiting the product's uses. Additional advantages of citrus fiber versus citrus flour are a higher total dietary fiber content (e.g., about 72-wt % versus 58-wt %); lower carbohydrate content (e.g., about 5-wt % versus 15-wt %); and higher water binding (e.g., greater than about 8.5 grams of water per gram of fiber versus 5.5 g/g). The protein content of the citrus fiber typically ranges from about 8 to 12wt-%.

The ratio soluble to insoluble dietary fiber is an important factor in the citrus fiber's functionality. Other important considerations include the degree of milling (granulometry) and drying conditions (process of drying). Generally, a higher degree of milling (i.e., a finer fiber granulometry) results in more smoothness of the fiber in the solution, as well as reduced water absorption capacity and reduced oil binding capacity compared to coarse fibers. Preferably dried citrus fruit fiber is obtainable according to the process disclosed in the pending WO patent application 2006/033697.

The vitamins, of the present invention, refer to the fat-soluble vitamins such as vitamin A, vitamin D, vitamin E, vitamin K and, mixtures thereof. Any pure or concentrated vitamin mixture can be used according to the present invention.

Also part of this invention is a composition where the weight ratio of citrus fruit fiber to hydrophobic vitamin is from about 1:0.001 to about 1:35, preferably 1:0.1 to 1:20, more preferably 1:0.6 to 1:10, and most preferably 1:1 to 1:4.

A preferred composition comprises from 0.001 to about 5 percent by weight of citrus fruit fiber, preferably 0.01 to 3%, and more preferably 0.05 to 1%.

Said composition can further comprise edible additives. These edible additives are selected from the group consisting of carbohydrates, proteins, peptides, amino acids, antioxidants, trace elements, electrolytes, intense sweeteners, edible acids, flavors, colorants, preservatives, and mixtures thereof.

The carbohydrates are selected from the group consisting of monosaccharides, disaccharides, gelling starches, starch hydrolysates, dextrins, fibers, polyols and mixtures thereof.

The monosaccharides include tetroses, pentoses, hexoses and ketohexoses.

Typical disaccharides include sucrose, maltose, trehalulose, melibiose, kojibiose, sophorose, laminaribiose, isomaltose, gentiobiose, cellobiose, mannobiose, lactose, leucrose, maltulose, turanose and the like.

Starch hydrolysates are produced by the controlled acid or enzymatic hydrolysis of starch and can be subdivided into two specific categories, maltodextrins and glucose syrups and are characterized by DE number (dextrose equivalent). In fact, DE number is a measurement of the percentage of reducing sugars present in the syrup and calculated as dextrose on a dry weight basis. Maltodextrins have a DE number up to 20 whereas glucose syrups have an DE number greater than 20.

Dextrins are prepared according to the dextrinisation method. Dextrinisation is a heat treatment of dry starch in presence or absence of acid.

Gelly starches may include emulsified starches such as starch n-octenyl succinate.

The low-calorie fibers can be polydextrose, arabinogalactan, chitosan, chitin, xanthan, pectin, cellulosics, konjac, gum Arabic, soy fiber, inulin, modified starch, hydrolysed guar, guar gum, beta-glucan, carageenan, locust bean gum, alginate, polyglycol alginate.

Among the major physiological electrolytes are sodium, potassium, chloride, calcium, and magnesium. Further trace elements can be included such as chromium, copper, selenium, iron, manganese, molybdenym, zinc and mixtures thereof.

The edible acids can be selected from phosphoric acid, citric acid, malic acid, succinic acid, adipic acid, gluconic acid, tartaric acid, fumaric acid and mixtures thereof.

An intense sweetener, which can be used as non-nutritive sweetener can be selected from the group consisting of aspartame, acesulfame salts such as acesulfame-K, saccharins (e.g. sodium and calcium salts), cyclamates (e.g. sodium and calcium salts), sucralose, alitame, neotame, steviosides, glycyrrhizin, neohesperidin dihydrochalcone, monatin, monellin, thaumatin, brazzein and mixtures thereof.

The flavors are selected from fruit flavors, botanical flavors and mixtures thereof. Preferred flavors are cola flavor, grape flavor, cherry flavor, apple flavor and citrus flavors such as orange flavor, lemon flavor, lime flavor, fruit punch and mixtures thereof. The amount of flavor depends upon the flavor or flavors selected, the flavor impression desired and the form of flavor used.

If desired, coloring agents can also be added. Any coloring agent approved for food use can be utilized for the current invention.

When desired, preservatives such as potassium sorbate and sodium benzoate can be added.

The edible liquid according to the present invention is selected from water, or water miscible liquid. Examples of water miscible liquid are milk, milk protein containing liquids, yoghurt, buttermilk, ice cream, soy milk based liquid, alcohol containing liquid, and the like.

Furthermore, the current invention relates to a process for preparing a liquid composition comprising an edible liquid, citrus fruit fiber and hydrophobic vitamin and said process comprises:

a. Adding dry citrus fruit fiber to an edible liquid to form a liquid mixture,
   b. Adding the hydrophobic vitamins to the liquid mixture,
   c. Treating mechanically the liquid mixture.

To form the liquid mixture of step a, any homogenization method can be used as the degree of hydration of the citrus fruit fiber is not highly critical.

Suitable mechanical treatment for step c is treatment with high-shear mixers, high-pressure valve homogenization, microfluidisation, high-power ultrasound and the like. By applying a strong shearing force, such as for example a high-pressure valve homogenizer, less dense fibre particles and increased thickening can be obtained.

The current invention relates to the use of the currently disclosed composition in food applications, feed applications, pharma products or cosmetics.

Said food applications are selected from the group consisting of beverages, dairy products, ice creams, sorbets and, desserts.

Said beverages include concentrates, gels, energy drinks, and carbonated beverages, non-carbonated beverages, syrups.

The beverage can be any medical syrup or any drinkable solution including iced tea, and fruit juices, vegetable based juices, lemonades, cordials, nut based drinks, cocoa based drinks, dairy products such as milk, whey, yogurts, buttermilk and drinks based on them.

Beverage concentrate refers to a concentrate that is in liquid form. The liquid concentrate can be in the form of a relatively thick, syrupy liquid.

The current invention further relates to beverages comprising citrus fruit fiber and hydrophobic vitamin, this composition being stable to coalescence during prolonged storage.

The current invention has the following advantages:

The composition, comprising citrus fruit fiber and hydrophobic vitamin, has a high nutritional value and is stable in aqueous dispersions, enhances the bioavailability of hydrophobic vitamins and, allows positive food labeling.

The invention is further defined by reference to the following examples describing in detail the preparation of the composition of the present invention. The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

COMPARATIVE EXAMPLE 1

Emulsification of Vitamin E a. Using Orange Pulp Fibre

| Orange pulp fibre stock solution (grams) | pH-7 Phosphate buffer (grams) | Vitamine E (grams) |
| --- | --- | --- |
| 250.0 | 247.5 | 2.5 |
| 250.0 | 245.0 | 5.0 |
| 250.0 | 240.0 | 10.0 |

The orange pulp fibre stock solution was prepared as follows: Orange pulp fibre (24 g; fine grade with an average dry powder size (volume mean diameter) of 103 p.m) was mixed into a pH-7 phosphate (0.15 M) buffer (1176 g) and left to hydrate at room temperature for 2 hours.

Aliquots (250 g) of this stock solution were mixed with the other ingredients using a high-shear mixer (Ultra-Turrax T25 with S25 N 25 F attachment) for 3 minutes at a low speed setting (1 or 2). A sample was taken (50 g) and the remainder homogenized at room temperature using a high-pressure valve homogenizer at 3000 psi.

In the emulsions, orange pulp fibre particles moved upwards during storage thereby leaving a clear layer at the bottom. The development of this clear layer was followed at 40° C. using a Turbiscan Lab Expert (Formulaction, France). The results listed in the Table below were obtained at a delta transmission threshold value of 20%.

Samples were stable for more than one day. The treatment and the ratio of orange pulp fiber to vitamin E affected the clear layer formation. Permanent stability was almost obtained when the emulsion was homogenized at an orange pulp fiber to vitamin E ratio of 1:1. Changes observed during storage were reversible. The initial state of the emulsion could be recovered simply by shaking the emulsion.

| Treatment | Orange pulp fibre:Vitamin E (g/g) | Clear layer formation at 40° C. | |
| --- | --- | --- | --- |
| | | Time (hrs) | Thickness (mm) |
| High-shear | 1:0.5 | 63 | 6.4 |
| High-shear | 1:1 | 81 | 6.4 |
| High-shear | 1:2 | 103 | 6.7 |
| Homogenization | 1:0.5 | 46 | 1.4 |
| Homogenization | 1:1 | 140 | 0.4 |
| Homogenization | 1:2 | 110 | 2.4 | b. Comparison: Using Octenyl Succinated Starch:

| nOSA Starch stock solution (grams) | pH-7 Phosphate buffer (grams) | Vitamine E (grams) |
| --- | --- | --- |
| 150.0 | 148.5 | 1.5 |
| 150.0 | 147.0 | 3.0 |
| 150.0 | 144.0 | 6.0 |

The octenyl succinated Starch stock solution was prepared as follows: nOSA starch (16 g; C*Emcap 12633, Cargill) was dissolved in a pH-7 phosphate (0.15 M) buffer (784 g) at 60° C. using a high-shear mixer (Ultra-Turrax T25 with S25 N 25 F attachment) for ca. 20 min. at a low speed setting (1 or 2).

Aliquots (150 g) of this stock solution were mixed with the other ingredients using the same high-shear mixer for 3 min. at a low speed setting (1 or 2). The mixture was then homogenized at room temperature using a high-pressure valve homogenizer at 3000 psi.

Within several hours of storage at 25° C., a white-colored ring formed on top of the emulsions. The development of this ring was followed using a Turbiscan Lab Expert (Formulaction, France). The results showed that this instability process was irreversible. The initial state of the dispersion could not be obtained by shaking the emulsions.

The invention claimed is:

1. A liquid composition comprising an edible liquid, citrus fruit fiber and a hydrophobic vitamin, wherein the weight ratio of citrus fruit fiber to hydrophobic vitamin is from about 1:1 to about 1:20, wherein the citrus fruit fiber comprises from 8 to 12% (w/w) proteins, has a total dietary fiber content of from 60 to 80% wt which comprises 45-50% soluble dietary fiber and 50-55% insoluble dietary fiber, and, in dried form, has a water binding capacity of from 7 to 25 (w/w).

2. A liquid composition according to claim 1 characterized in that the hydrophobic vitamin is chosen from the group consisting of vitamin A, D, E, K and mixtures thereof.

3. A liquid composition according to claim 1 characterized in that the hydrophobic vitamin is vitamin E.

4. A liquid composition according to claim 1 characterized in that the edible liquid is selected from water or water-miscible liquid.

5. A liquid composition according to claim 1 characterized in that the citrus fruit fiber has a total dietary fiber content of from 60 to 80% wt and, in dried form, a water binding capacity of from 7 to 12 (w/w).

6. A liquid composition according to claim 1 characterized in that the citrus fruit fiber is obtained from citrus fruit selected from the group consisting of oranges, tangerines, limes, lemons, and grapefruit.

7. A liquid composition according to claim 1 characterized in that the composition further comprises edible additives.

8. A liquid composition according to claim 1 wherein the citrus fiber is in dry form before being added to the edible liquid.

9. Beverage comprising the liquid composition according to claim 1.

10. A cosmetic product comprising the liquid composition according to claim 1.

11. The liquid composition of claim 1, wherein the ratio of citrus fruit fiber to hydrophobic vitamin is from about 1:1 to about 1:10.

12. A process for preparing a composition comprising an edible liquid, citrus fruit fiber and hydrophobic vitamin, said process comprises:
   a. adding dry citrus fruit fiber to an edible liquid to form a liquid mixture, wherein the citrus fruit fiber comprises from 8 to 12% (w/w) proteins, has a total dietary fiber content of from 60 to 80% wt which comprises 45-50% soluble dietary fiber and 50-55% insoluble dietary fiber, and, in dried form, has a water binding capacity of from 7 to 25 (w/w),
   b. adding the hydrophobic vitamins to the liquid mixture, wherein the weight ratio of citrus fruit fiber to hydrophobic vitamin is from about 1:1 to about 1:20, and
   c. treating, mechanically, the liquid mixture.

* * * * *

UNITED STATES PATENT AND TRADEMARK OFFICE
CERTIFICATE OF CORRECTION

PATENT NO. : 8,647,689 B2  
APPLICATION NO. : 11/993347  
DATED : February 11, 2014  
INVENTOR(S) : Jozef Guido Roza Vanhemelrijck et al.

Page 1 of 1

It is certified that error appears in the above-identified patent and that said Letters Patent is hereby corrected as shown below:

On the Title Page, Item (56), in column 2, under "OTHER PUBLICATIONS", lines 8-9, delete "PCT/U52010/024015" and insert -- PCT/US2010/024015 --, therefor.

Signed and Sealed this  
Tenth Day of June, 2014

Michelle K. Lee  
*Deputy Director of the United States Patent and Trademark Office*